(12) United States Patent
Miller

(10) Patent No.: US 7,052,902 B2
(45) Date of Patent: May 30, 2006

(54) CONTINUOUSLY OPERATIONAL BIOLOGICAL REACTOR

(76) Inventor: Russell Holt Miller, 2830 - 8th Ave., SE., Naples, FL (US) 34117

( * ) Notice: Subject to any disclaimer, the term of this patent is extended or adjusted under 35 U.S.C. 154(b) by 312 days.

(21) Appl. No.: 10/690,962

(22) Filed: Oct. 23, 2003

(65) Prior Publication Data
US 2005/0089998 A1   Apr. 28, 2005

(51) Int. Cl.
C12M 1/02 (2006.01)

(52) U.S. Cl. .................. 435/290.3; 435/290.4

(58) Field of Classification Search ............. 435/290.3
See application file for complete search history.

(56) References Cited

U.S. PATENT DOCUMENTS

| | | | |
|---|---|---|---|
| 3,248,175 A | 4/1966 | Emmet | |
| 3,890,129 A | 6/1975 | Chester | |
| 3,960,537 A | 6/1976 | Kaelin | |
| 4,042,219 A | 8/1977 | Terry | |
| D352,580 S | 11/1994 | Cook | |
| 5,432,088 A | 7/1995 | Kakuk et al. | |
| 5,545,560 A * | 8/1996 | Chang | 435/290.2 |
| 5,945,332 A * | 8/1999 | Fors | 435/262 |
| 6,132,601 A * | 10/2000 | March et al. | 210/150 |

* cited by examiner

Primary Examiner—David Redding
(74) Attorney, Agent, or Firm—Theresa M. Seal

(57) ABSTRACT

A continuously operational biological reactor for the aerobic processing of animal waste into chemically free fertilizer includes an inner drum and an outer drum coaxially mounted on a horizontal center shaft with the inner annular surface of each drum including conveyor threads with the angularity of the conveyor threads being opposite each other so that the animal waste material can be conveyed down the inner drum and then back up the outer drum for processing into chemically free fertilizer. The biological reactor will include a hopper for receiving the material, a dewatering unit for material compression and preheater, and a mixer for introducing air and microbes to facilitate the processing. The center shaft includes instrumentation passageways for monitoring and control of the process and air flow passageways for diluting and discharging volatile substances such as methane.

12 Claims, 5 Drawing Sheets

CONTINUOUSLY OPERATIONAL BIOLOGICAL REACTOR

FIELD OF THE INVENTION

The present invention pertains to digester tanks and reactors, and, more particularly pertains to a continuously operational double drum biological reactor for environmentally safe aerobic decomposition of bulk animal and livestock waste.

BACKGROUND OF THE INVENTION

Farm animals and farm livestock, such as cattle, sheep, goats, and pigs, produce tens of millions of tons of waste each year. The disposal of such waste presents both problems and opportunities for farms and farmers ranging from the small family owned generational farm to the large corporate farms and for the feed livestock yards and food processing plants. The opportunity that presents itself is that if properly treated such waste can be transformed into valuable fertilizer for enhancing crop productivity and yields for that particular farm; or as a commodity that can be sold for profit. The ability to transform livestock waste into a salable commodity is of particular importance for small family-type farms whose profit margin is slight and tenuous. The problem faced by farms of all types is that local, state and federal laws, from township zoning ordinances to federal EPA and USDA regulations regulate and control the treatment, removal, disposal, reuse and recycling of animal waste. Numerous regulations and standards must be adhered to before, for example, livestock manure can be reprocessed for sale and use as natural fertilizer.

The prior art discloses a number of different tanks and drums for decomposing and processing waste and refuse material into useful soil fertilizer.

For example, the Emmet patent (U.S. Pat. No. 3,248,175) discloses a rotatable drum for manufacturing compost that includes a plurality of spaced openings at one end surface of the drum that can be selectively opened or closed to allow the discharge of the warm moist air or the air-steam mixture being piped through the drum. The conduit for the air extends in a u-shaped manner within the drum.

The Chester patent (U.S. Pat. No. 3,890,129) discloses a composting device that has open mesh side and end panels. For aerobic treatment, removable covers are placed over the open mesh side panels and when composting is completed, the covers are removed so that the composted material can be discharged through the mesh panels. For anaerobic treatment, both the mesh side panels and ends are covered to restrict airflow for such anaerobic treatment.

The Kaelin patent (U.S. Pat. No. 3,960,537) discloses a method and device for treating refuse and sludge and includes a chamber having an upper inlet aperture for receiving the material to be treated and a lower outlet aperture for discharge of the material. Sets of gas distributor blades are axially disposed along a vertical shaft for introducing a gas mixture into the chamber for treating the material.

The Terry patent (U.S. Pat. No. 4,024,219) discloses a drum for aerobic processing of waste material and includes a chamber through which a horizontal shaft extends, and projecting from the shaft are three vanes for effecting mixing and processing of the material.

The Cook patent (U.S. design Pat. No. 352,580) discloses a double drum design wherein two drums are mounted on a stand side-by-side for composting material.

The Kakuk et al. patent (U.S. Pat. No. 5,432,088) discloses a bin for aerobic composting that includes a plurality of horizontal mixing and aeration slots through which an implement, such as a garden tool, can be inserted for effecting the mixing of the material held within the bin.

Despite the ingenuity of the above devices, there remains a need for a continuously operable aerobic digester that can expedite the process of transforming waste material continually fed therein to safe and useful fertilizer.

SUMMARY OF THE INVENTION

The present invention comprehends a continuously operable biological reactor for processing animal waste material into environmentally safe, chemically free natural fertilizer and includes a pair of drums, specifically an inner drum and an outer drum coaxially mounted on a horizontally extending center shaft for aerobic processing of animal waste material by continually moving animal waste material through the inner drum in one direction and then through the outer drum in the opposite direction. Each drum includes a series of conveyor threads or flights for turning over and moving the material therethrough, with the conveyor threads of each drum being angled in the opposite direction so that the waste material can move down the inner drum and then back up the outer drum in the opposite direction. The biological reactor also includes a dewatering press for removing excess water from the material received from a hopper, a mixer wherein microbes are introduced to facilitate material processing and a heater for directing a continuous airflow into both drums while the center shaft includes passageways for control and monitoring instrumentation and airflow passageways.

It is an objective of the present invention to provide a continuously operational reactor for digesting animal waste matter using a screw-type conveyance design.

It is another objective of the present invention to provide a continuously operational reactor wherein the animal waste matter is quickly brought to the aerobic state for processing by a pair of coaxially mounted rotatable drums.

It is yet another objective of the present invention to provide a continuously operational biological reactor having a center shaft on which processing drums are mounted and through which instrumentation and airflow can be directed.

It is still another objective of the present invention to provide a continuously operational biological reactor wherein animal waste material is input and environmentally safe fertilizer is output that meets all state and federal guidelines and regulations.

It is still yet another objective of the present invention to provide a continuously operational biological reactor that processes animal waste into chemically-free fertilizer thereby decreasing the pollution of ponds, rivers, and water tables from the uncontrolled runoff, decay and degeneration of animal waste.

Still another objective of the present invention is to provide a continuously operational biological reactor that is able to process canning factory waste into chemically free, environmentally safe fertilizer for sale or farm use.

Still yet another objective of the present invention is to provide a continuously operational biological reactor capable of processing the waste product generated in the milking area of a diary farm into useful, environmentally safe fertilizer.

Still yet a further objective of the present invention is to provide a continuously operational biological reactor that is transportable within a container to different sites, and is capable of processing one ton of animal waste an hour and up to 24 tons of animal waste daily.

A yet further objective of the present invention is to provide a continuously operational biological reactor that allows for on site processing and treatment of waste material thereby avoiding the cost and time of transporting such waste to a dump site or landfill.

These and other objects, features and advantages will become apparent upon a perusal of the following detailed description when read in conjunction with the drawings and appended claims.

DETAILED DESCRIPTION OF THE PREFERRED EMBODIMENT

Illustrated in FIGS. 1–6 is a continuously operable biological digester or reactor 10 for treating and processing animal waste, primarily from farm and livestock animals, into a natural fertilizer that is chemical free and environmentally safe and approved by the relevant government agencies. By treating and processing the animal waste (predominantly animal excrement) on site, the pollution of soil, streams, lakes, rivers and aquifers from seepage and runoff of the animal waste is prevented; and a salable commodity is produced for the farmer or other user of the reactor 10.

As shown in FIGS. 1–6, the biological reactor 10 includes an external housing or frame 12 preferably of black iron. Mounted at a first end of the frame 12, and extending into the frame 12, is a hopper 14 into which the animal waste is dumped from a conveyor or other piece of machinery such as a back hoe or ditch digger. The hopper 14 can include some type of screen or scrubber for removing or breaking down sticks, rocks and other non-digestible material intermingled with the animal waste. The hopper 14 is connected to a dewatering device 16 that is preferably an agricultural press operating at 120 psi; the dewatering device 16 compresses the animal waste for removing excess water from the waste and it is also where the preheating of the animal waste occurs. A worm conveyor (not shown) extends through the dewatering device 16 and acts on the animal waste passing through the dewatering device 16.

Figure 1:
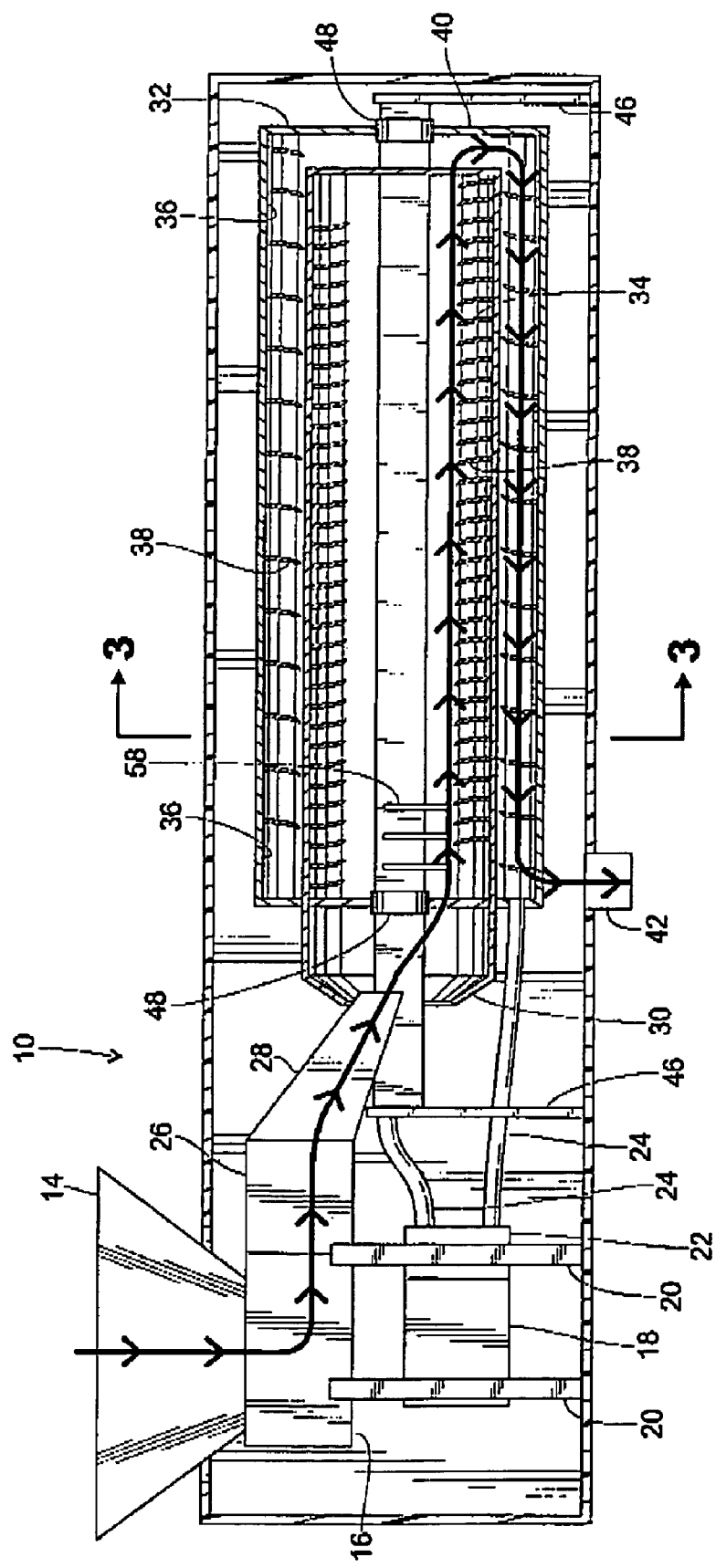
FIG. 1 is a sectioned elevational view of the continuously operational biological reactor of the present invention illustrating the movement of animal waste material through the inner drum and then the outer drum.
Figure 4:
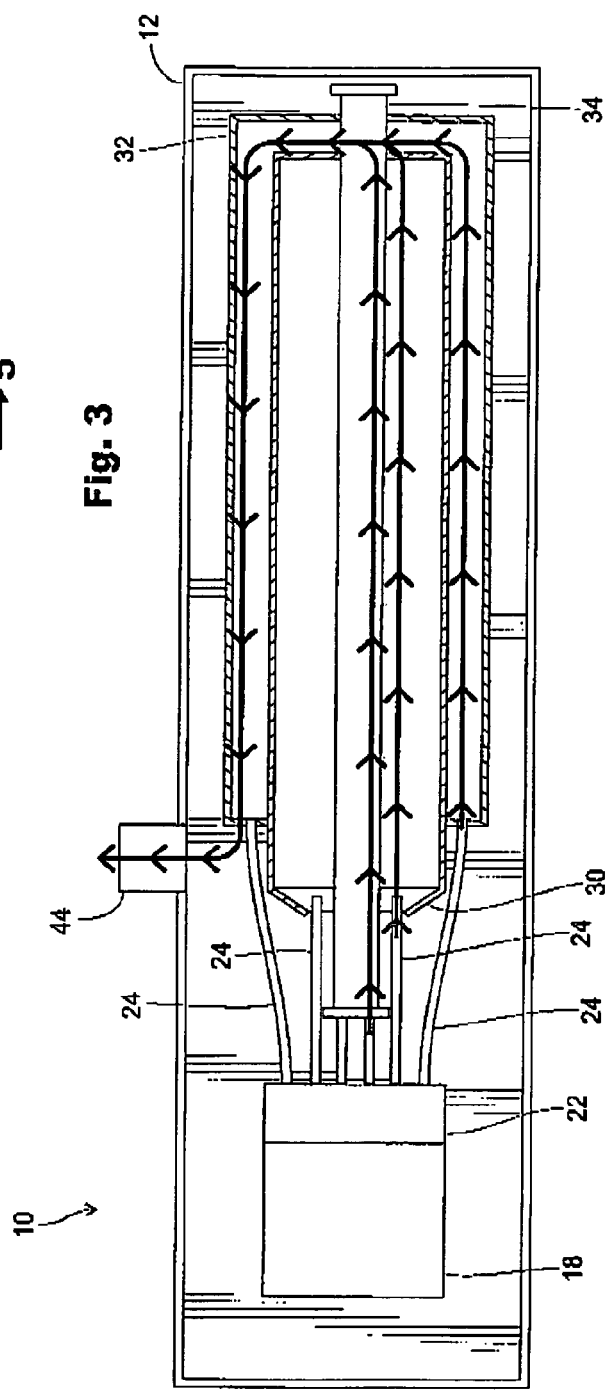
FIG. 4 is a bottom plan view of the continuously operational biological reactor illustrating the air flow pattern through the inner drum, the outer drum, and the center shaft.

Illustrated in FIGS. 1 and 4 is a furnace 18 that is preferably a 100 BTU heater with a three-speed fan or blower. The furnace 18 is mounted to the inside of the frame 12 by means of struts or support members 20. Attached to the furnace 18 is a plenum chamber 22 for directing the flow of air from the furnace 18 into air ducts 24 extending outwardly from the plenum chamber 22. The purpose of the airflow (shown by the directional arrows of FIG. 4) is to dilute and discharge the methane that is a constituent and by-product of the animal waste, and to keep the methane—and other gasses—moving through the reactor 10 as will be hereinafter further explained. Adjoined to the dewatering device 16 is a mixer 26, and as the animal waste is conveyed through the mixer 26, microbes are introduced to facilitate the breakdown and decomposition of the animal waste. In addition, air is introduced into the mixer 26 for intermixing with the animal waste and for providing the aerobic processing conditions.

Figure 2:
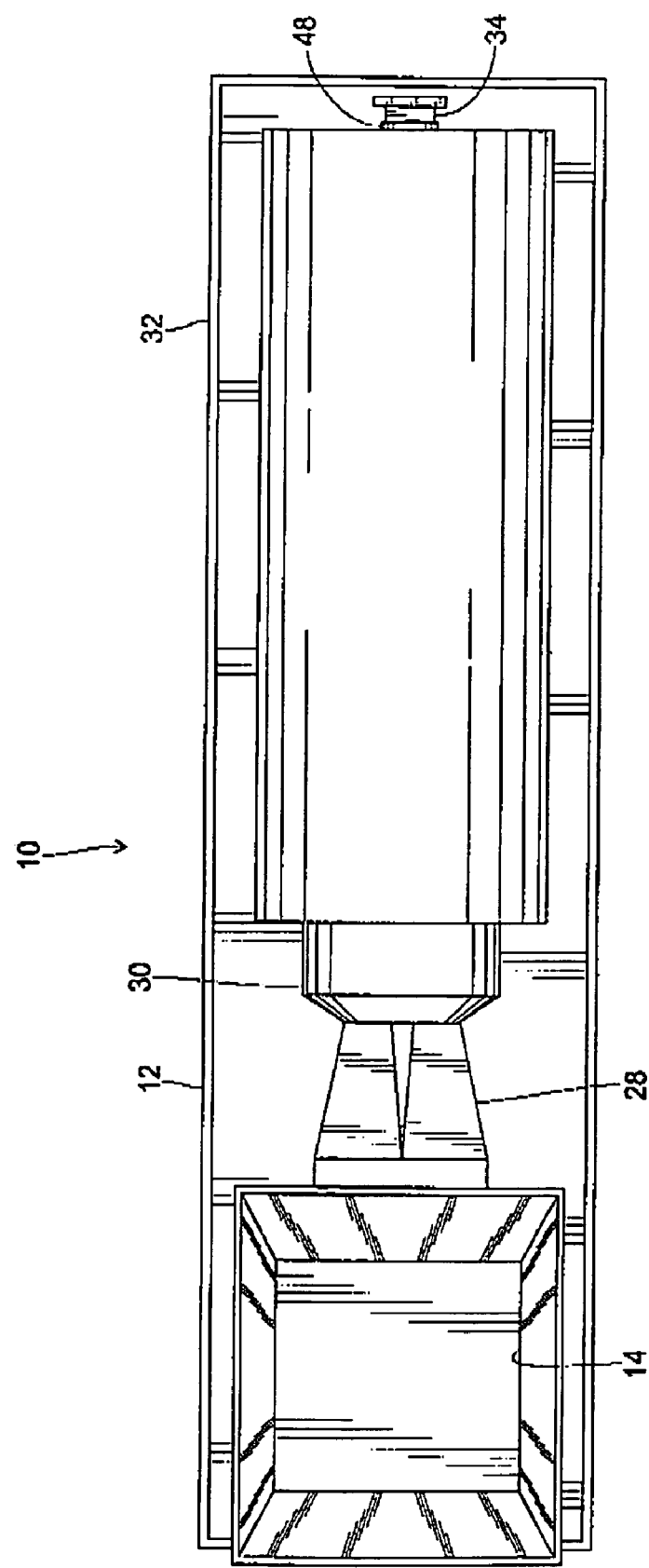
FIG. 2 is a top plan view of the continuously operational biological reactor of the present invention illustrating the location of the hopper, the chute and the inner an outer drum.

As illustrated in FIGS. 1 and 2, attached to the mixer 26 and angled downwardly therefrom is a double-chambered chute 28. The animal waste downwardly descends within both chambers of the chute 28, and the chute 28 will include a back pressure plate that will operate as a safety valve if excessive pressure differentials occur within the reactor 10. The chute 28 communicates with the two primary components of the reactor 10: an inner reactor drum 30 and an outer reactor drum 32. Both the inner drum 30 and the outer drum 32 are coaxially mounted to a center shaft 34, and air ducts 24 interconnect the center shaft 34 to the furnace 18 so that airflow can be directed through the center shaft 34 and to the drums 30 and 32. The drums 30 and 32 can be manufactured from stainless steel or from fiberglass and each drum 30 and 32 includes an inner annular surface 36. The inner drum 30 and the outer drum 32 include a plurality of conveyor flights or threads 38 secured, preferably by welding, to their respective inner annular surfaces 36; and the conveyor threads 38 extend along the entire inside annular surface 36 of each respective drum 30 and 32. The conveyor threads 38 for each drum 30 and 32 project inwardly from each respective inner surface 36 at least 12 inches and to facilitate the movement of the animal waste through, first, the inner drum 30, and then the outer drum 32, the conveyor threads 38 for the inner drum 30 are set at an angle that is opposite of the conveyor threads 38 of the outer drum 32. The inner drum 30 has a first ingress end that registers with the double-chambered chute 28 for receiving the animal waste, and an opposite egress end having at least one discharge aperture 40 through which animal waste flows for processing within the outer drum 32. In addition, air ducts 24 register with the outer drum 32 to maintain the flow of air therethrough. When the treatment and processing of the animal waste is completed, the treated waste flows through an outlet 42 for discharging and transferring to, for example, a waiting conveyor, bagging unit or dump truck. In addition, an air vent 44 for externally venting air, and especially the methane gas, can be included as shown in FIG. 4.

Figure 3:
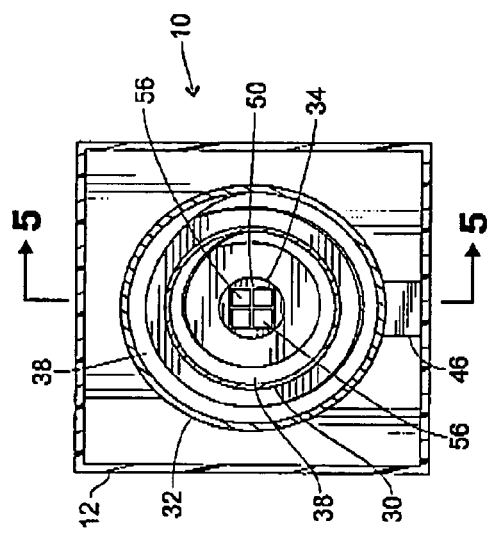
FIG. 3 is a sectioned elevational view of the continuously operational biological reactor taken along line 3—3 of FIG. 1 illustrating the coaxial alignment of the inner and outer drums on the center shaft.
Figure 5:
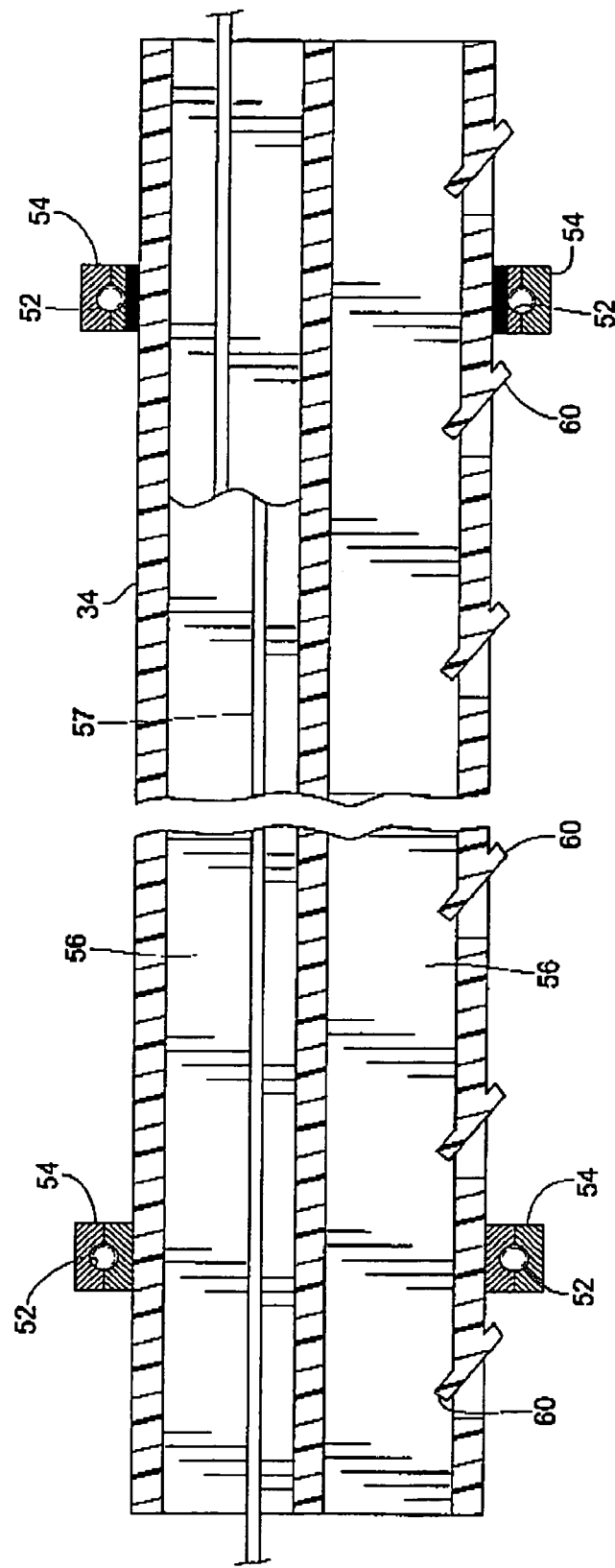
FIG. 5 is a sectioned elevational view taken along lines 5—5 of FIG. 3 illustrating the instrumentation and air flow passageways extending through the center shaft.
Figure 6:
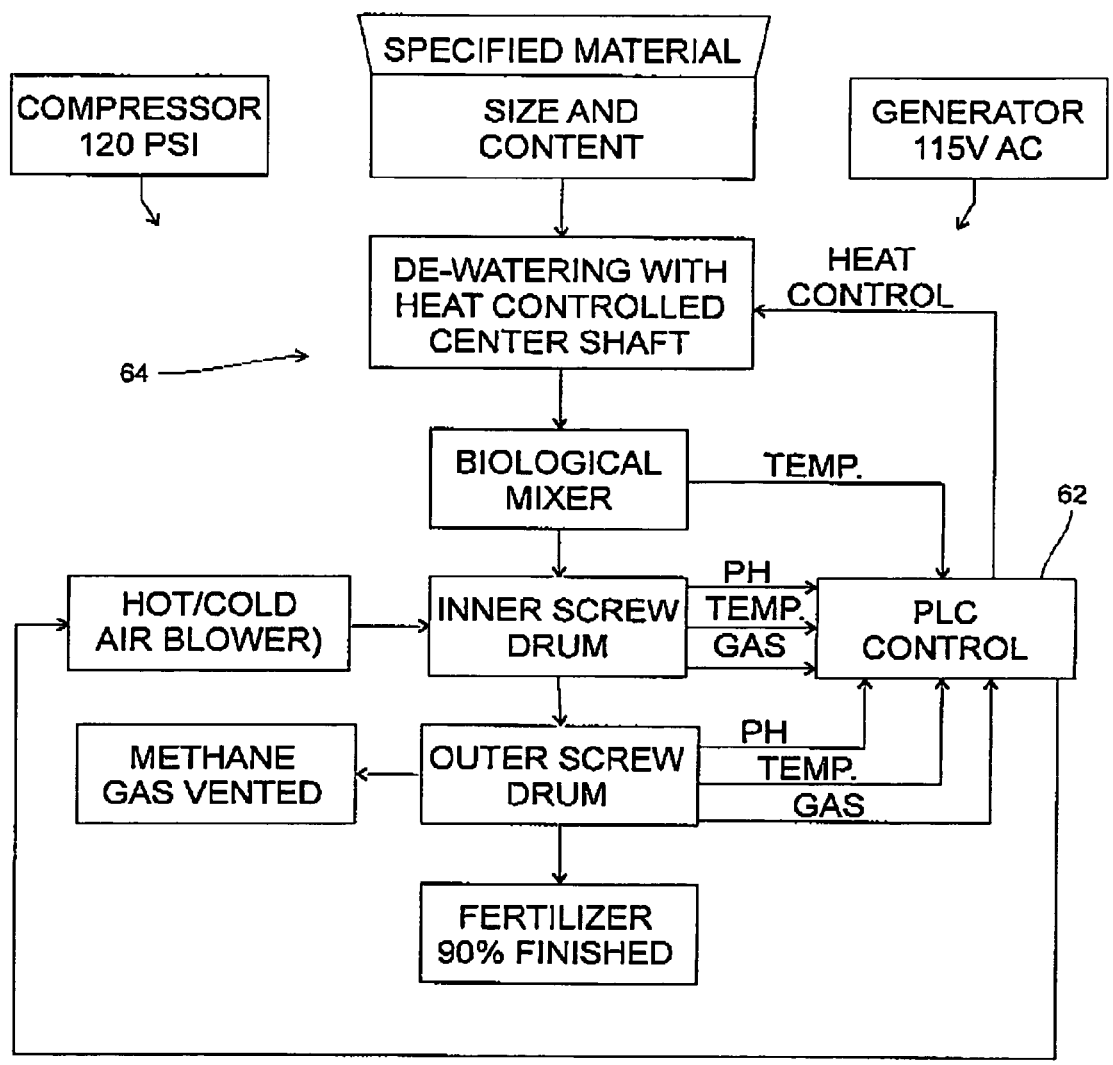
FIG. 6 is a basic flow chart illustrating the control and monitoring events that occur concomitant with the movement of the waste material through the biological reactor.

As shown in FIGS. 1–5, the center shaft 34 is mounted to the inside of the frame 12 by shaft mounting members 46, and the center shaft 34 extends through both the inner and outer drums 30 and 32 so that both drums 30 and 32 can rotate simultaneously and continuously thereon. The center shaft 34 includes bearing housings 48 located at opposed ends of the shaft 34, and enclosed within the respective bearing housings 48 are machined bearing plates 50 and associated roller bearings 52; FIG. 5 shows the bearings 52 and bearing blocks 54. In addition, as shown in FIGS. 3 and 5, the center shaft 34 (preferably manufactured from steel tubing) includes passageways 56 for accommodating instrumentation and airflow, and the passageways 56 are coextensive with the shaft 34. The center shaft 34 of the present invention includes four passageways 56, two upper passageways for carrying instrumentation 57 and two lower passageways serving as airflow conduits. Also, instrumentation probes 58 are mounted to the center shaft 34 and extend into the interior of at least the inner drum 30 for monitoring such physical variables as temperature, ph levels, and gas content within the reactor 10. At least six instrumentation probes 58 will be mounted to the center shaft 34 in the present embodiment of the invention. The center shaft 34 also includes a small space for accommodating a high pressure water conduit having spray nozzles spaced along the length of the conduit for discharging cleaning water through the nozzles and into the drums 30 and 32 for cleaning out the drums 30 and 32. Moreover, the center shaft 34 is interconnected to the furnace 18 and plenum chamber 22 by air ducts 24, as shown in FIG. 4, and spaced along the center shaft 34 are air shaft vents 60 for directing airflow from the center shaft 34 into the inner drum 30.

Various drive or drum rotation means can be used with the reactor 10, and a preferred drive means includes 20 hp variable speed motor appropriately geared down for rotating both drums 30 and 32 at the rate of three revolutions per hour for continuously turning the animal waste and moving the animal waste through both drums 30 and 32. Power for the motor can be supplied from an appropriately rated electrical outlet or from an optional generator. A PLC controller 62 will monitor and control the various functions and parameters of the reactor 10, such as the ph balance, the temperature, and the gas levels, throughout the processing steps shown in the processing flowchart 64 of FIG. 6.

In operation animal waste would be dumped into the hopper 14 where sticks and rocks would be screened for removal or broken up for digesting by screeners and/or scrubbers. For maximum digesting efficiency material should not exceed two inches in length or diameter. The animal waste is then compressed and preheated by the dewatering device 16 and then the animal waste enters the mixer 26 where the microbes are introduced for decomposing the animal waste by natural means. Air is also injected in the mixer 26 for providing the aerobic element to the processing of the animal waste. Thus, the animal waste is preheated and brought up quickly to the aerobic state whereby the ph and temperature are monitored and controlled by the PLC controller 62 (which can be from an external manually operable panel of known construction) to maintain the preheated aerobic state before the animal waste descends through the chute 28 and into the inner drum 30. The flow of air from the furnace 18 and plenum chamber 22, through the air ducts 24, and then through the inner drum 30 and the outer drum 32 dilutes and discharges the methane so that the methane's flammability is nullified. The flow of air through the center shaft 34 occurs simultaneous with the airflow through the inner and outer drums 30 and 32. The animal waste moves through the inner drum 30 by the rotatable action of the conveyor threads 38, and as the animal waste moves through the inner drum 30, the PLC controller 62 monitors events in the dewatering device 16, the furnace 18 and the mixer 26 so that the proper temperature and ph balance is maintained before the animal waste enters the inner drum 30.

The movement of animal waste from the hopper 14 and through the inner drum 30 and then in the reverse direction through the outer drum 32 is shown by the directional arrows of FIG. 1. The outer drum 32 is the slower digesting drum and thus the animal waste has a longer dwell time while going through the outer drum 32. The slower digesting of the outer drum 32 allows for a cooling down of the waste as the temperature is carefully monitored to allow for the gradual cooling of the animal waste before discharge from the outer drum 32. Both the inner and outer drums 30 and 32 turn the animal waste at three revolutions per hour, and generally more solid material moves into the outer drum 32 from the inner drum 30: for example, if 10% of the material is solid entering the inner drum 30, the material is approximately 38–45% solid as it is discharged from the inner drum 30 to the outer drum 32. The approximate weight of the animal waste is 66 pounds per cubic foot, and the configuration of the drums 30 and 32 provides for a discharge of 30 cubic feet of material from each drum 30 and 32 per hour thereby providing for the production of one ton of natural fertilizer per hour. It should be note that the biological reactor 10 of the present invention will not work with any material that will kill the biological microbes such as material from the family of hydrocarbon compounds. Thus, the present invention is a continuously operable biological reactor 10 in contrast to batch processors that go from anaerobic to aerobic and then back to anaerobic processing states.

It will be seen that a preferred embodiment of the invention is disclosed, and that those skilled in the art will recognize that numerous alterations, modifications, and variations can be made that will still fall within the scope of the above detailed description and the following appended claims.

I claim:
1. A continuously operational biological reactor for processing animal waste into natural fertilizer, comprising:
   a portable frame;
   an outer drum mounted within the frame and having a plurality of conveyor threads spaced along an interior annular outer drum surface of the outer drum;
   an inner drum mounted within the frame and partially enclosed by the outer drum and having a plurality of conveyor threads spaced along an interior annular inner drum surface;
   the inner drum being in flow communication with the outer drum so that animal waste can move through the inner drum and then the outer drum for processing into natural fertilizer;
   the conveyor threads for the outer drum being set at an angle that is opposite of the angle of the conveyor threads for the inner drum;
   a hopper for receiving the animal waste and for directing the animal waste to the inner drum;
   means for compressing and preheating the animal waste received from the hopper;
   means for introducing biological microbes into the animal waste received from the means for compressing and preheating the animal waste;
   air flow injection means for producing a continuous flow of air into the inner drum and the outer drum for moving, diluting and discharging noxious gases that accompanying the animal waste;
   a center shaft extending through the inner drum and the outer drum so that both the inner drum and the outer drum can be coaxially mounted thereon, the center shaft being in air flow registration with the air flow injection means so that a continuous flow of air can be maintained within and through the inner drum and the outer drum; and
   control means interconnected to the center shaft for monitoring and controlling the processing of the animal waste within the inner drum and the outer drum and for monitoring and regulating the physical parameters of ph balance, temperature and gas content within the reactor.

2. The continuously operational biological reactor of claim 1 wherein the means for compressing and preheating the animal waste is a dewatering device that is positioned beneath the hopper and in flow communication therewith.

3. The continuously operational biological reactor of claim 2 wherein the means for introducing biological microbes into the animal waste is a mixer connected to the dewatering device and in flow communication therewith.

4. The continuously operational biological reactor of claim 3 wherein the inner drum and the outer drum turn at three revolutions per hour.

5. The continuously operational biological reactor of claim 4 further comprising a plurality of instrumentation probes mounted to the center shaft and extending into the inner drum for providing the control means with information on the physical parameters of ph balance, temperature, and gas content of the animal waste moving through the inner drum and the outer drum.

6. The continuously operational biological reactor of claim 5 wherein the inner drum and the outer drum are both capable of discharging at least 30 cubic feet of animal waste during each hour of operation.

7. A continuously operational aerobic biological reactor for processing animal waste into natural fertilizer, comprising:
   a transportable frame;
   an outer drum mounted within the frame and having a plurality of conveyor threads spaced along an interior annular surface of the outer drum;
   an inner drum mounted within the frame and partially encompassed by the outer drum and having a plurality of conveyor threads spaced along an interior annular surface of the inner drum;
   the inner drum being in flow communication with the outer drum so that animal waste can move through the inner drum and then through the outer drum for processing into natural fertilizer;
   the conveyor threads of the outer drum being disposed at an angle that is opposite of the angle of the conveyor threads of the inner drum;
   a hopper for receiving the animal waste and for directing the animal waste to the inner drum;
   a dewatering unit for compressing and preheating the animal waste received from the hopper;
   a mixer for introducing biological microbes into the animal waste to facilitate the aerobic decomposition of the animal waste;
   air flow injection means for maintaining a continuous flow of air within the inner drum and the outer drum in order to move, dilute and discharge noxious gases that accompany the animal waste;
   a center shaft extending through the inner drum and the outer drum so that both drums can be coaxially mounted thereon, the center shaft being in air flow registration with the air flow injection means so that a continuous flow of air can be maintained within and through the inner drum and the outer drum; and
   control means interconnected to the center shaft for monitoring and controlling the processing of the animal waste within the inner drum and the outer drum and for monitoring and regulating the physical parameters of ph balance, temperature, and gas content within the inner drum and the outer drum.

8. The continuously operational biological reactor of claim 7 wherein the inner drum and the outer drum both turn at three revolutions per hour.

9. The continuously operational biological reactor of claim 8 further comprising a plurality of instrumentation probes mounted to the center shaft and extending into the inner drum for providing the control means with information on the physical parameters of ph balance, temperature, and gas content.

10. The continuously operational biological reactor of claim 9 wherein the inner drum and the outer drum are both capable of processing at least 30 cubic feet on animal waste during one hour of operation and up to 24 tons of animal waste through one day of continual processing.

11. The continuously operational biological reactor of claim 10 wherein the center shaft includes a plurality of coextensive passageways for accommodating instrumentation and air flow.

12. The continuously operational biological reactor of claim 11 wherein the center shaft includes a plurality of air shaft vents for directing the flow of air from the passageways and into the inner drum.

* * * * *